(12) United States Patent
Hu et al.

(10) Patent No.: US 6,544,954 B1
(45) Date of Patent: Apr. 8, 2003

(54) STABLE GALACTOSE INJECTION SOLUTIONS

(75) Inventors: Oliver Yoa-Pu Hu, 2F, No.81, Alley 5, Lane 24, Sec. 3, Ting-Chou Road, Taipei (TW); Cheng-Huei Hsiong, Taipei (TW)

(73) Assignee: Oliver Yoa-Pu Hu, Taipei (TW)

( * ) Notice: Subject to any disclaimer, the term of this patent is extended or adjusted under 35 U.S.C. 154(b) by 0 days.

(21) Appl. No.: 10/076,650

(22) Filed: Feb. 19, 2002

(51) Int. Cl.$^7$ .................. A61K 31/70; C07H 17/00; A01N 25/00
(52) U.S. Cl. .................. 514/25; 536/1.11; 536/4.1; 514/23; 514/893
(58) Field of Search ............... 514/23, 25; 536/1.11

(56) References Cited

U.S. PATENT DOCUMENTS

| | | |
|---|---|---|
| 4,010,251 A | 3/1977 | Green |
| 5,723,121 A | 3/1998 | Takenaga et al. |
| 6,071,245 A | 6/2000 | Kohno et al. |
| 6,177,274 B1 | 1/2001 | Park et al. |

OTHER PUBLICATIONS

Oliver Yoa–Pu Hu et al.; Novel Galactose Single Point Method as a Measure of Residual Liver Function: Example of Cefoperazone Kinetics in Patients with Liver Cirrhosis; J Clin Pharmacol, 1995, p 250–258, vol. 35.

Oliver Yoa–Pu Hu et al.; Guest Editor's Note: Practical and Regulatory Issues on New Drug, New Dosage Form, and Generic Drug Development Drug Information Journal, 1997, p. 1145–1147, vol. 31.

Oliver Yoa–Pu Hu et al.; Determination of Galactose in Human Blood by High–Performance Liquid Chromatography: Comparison with an Enzymatic Method and Application to the Pharmacokinetic Study of Galactose in Patients with Liver Dysfunction; Journal of Pharmaceutical Sciences, 1995, p. 231–235, vol. 84, No. 2.

Oliver–Yoa–Pu Hu et al.; Pharmacokinetics of Promazine in Patients with Hepatic Cirrhosis–Correlation with a Novel Galactose Single Point Method; Journal of Pharmaceutical Sciences, 1995, p. 111–114, vol. 84, No. 1.

Vijay O. Bhargava et al.; Stability of galactose in aqueous solutions; American Journal of Hospital Pharmacy, 1989, p. 104–108, vol. 46.

Hung–Shang Tang et al.; Assessment of Liver Function Using a Novel Galactose Single Point Method; Digestion, 1992, p. 222–231, vol. 52.

*Primary Examiner*—James O. Wilson
*Assistant Examiner*—Ganapathy Krishnan
(74) *Attorney, Agent, or Firm*—Fei-Fei Chao; Venable, Baetjer, Howard & Civiletti, LLP

(57) ABSTRACT

The present invention provides stable galactose injection solutions, which contain 1 to 50% by weight of galactose, 0.01 to 1 M of a buffer solution, and 0.01 to 5% of an antioxidant. The preferred buffer solution is citrate buffer. The preferred anti-oxidant is sodium bisulfite. The galactose injection solution of the present invention has a pH between 4.0 and 9.0 and is stable at 80° C. for at least 2 weeks.

13 Claims, 6 Drawing Sheets

STABLE GALACTOSE INJECTION SOLUTIONS

FIELD OF THE INVENTION

The present invention relates to stable galactose injection solutions for injection, which demonstrates high stability after storage at 80° C. for two weeks. The galactose injection solutions contain (1) 1 to 50% by weight of galactose, (2) a buffer solution, and (3) an antioxidant, and are at pH of 4.0 to 9.0. The preferred buffer solution is citrate buffer, preferably at a concentration of 0.01 M to 1.0 M. The preferred antioxidant is sodium bisulfite, preferably at a concentration of 0.001 to 5% by weight.

BACKGROUND OF THE INVENTION

Galactose, the $C_4$-epimer of glucose, has been widely used for diagnostic and nutritional purposes. Galactose is one of the hexoses in lactose. Galactose resembles glucose in chemical structure, yet galactose differs greatly from glucose in other physical and chemical properties, such as solubility and stability.

Galactose has been widely used to assess liver function based on its enzymatic biotransformation to glucose, and as a nutrient for glucose-intolerant neonates. During the preparation of galactose solution, the solution is sterilized by autoclaving which causes the degradation of galactose to form 5-hydroxymethylfurfural (5-HMF) accompanied by development of amber to yellow coloration.

Galactose has a high affinity for the liver parenchymatous cells, which makes galactose useful for evaluating liver function. U.S. Pat. No. 4,010,251 discloses a composition of a scanning agent for imaging liver which contains a galactose moiety; U.S. Pat. No. 5,723,121 discloses an interferon having at least one galactose residue which composition has an improved accumulation in the liver and is preferably intravenously injected; U.S. Pat. No. 6,071,245 discloses the use of radioactive galactose in food as diagnostic agent for liver function; U.S. Pat. No. 6,177,274 discloses a compound for gene delivery targeted at liver which has galactose as a preferred targeting moiety.

However, galactose injection is generally prepared extemporaneously by pharmacists, particularly due to the unstable nature of the galactose solution and the absence of stability information regarding galactose injection solutions.

Bhargava et al., *Am. J. Hosp. Pharm.*, 46: 104–108 (1989), have tested the stability of galactose formulations and suggested that galactose degradation increases in relation to the increase of its concentration, temperature, and buffer concentration. Bhargava et al. proposes that galactose solution should be better kept in distilled or sterile water and the galactose solution containing pH buffer should not be sterilized by autoclaving, or it would cause significant discoloration of the solution.

Also, as indicated in Bhargava et al., many commercially supplied galactose may be pyrogenic and microbial contaminated. Thus, it is important to find galactose formulations which are pH balanced and can sustain sterilization by autoclaving while not affecting the purity and stability of galactose.

SUMMARY OF THE INVENTION

The present invention provides galactose injection solutions, which demonstrate high stability after sterilization by autoclaving and storage at 80° C. for at least two weeks.

The galactose injection solutions of the present invention contain 1–50% galactose, a buffer solution and an anti-oxidant, and are at a pH of 4.0 to 9.0. Examples of the buffer solution include, but are not limited to, citrate buffer, phosphate buffer, acetate buffer, carbonate buffer, and triethanolamine buffer. The preferred buffer solution is citrate buffer. Examples of the anti-oxidant include, but are not limited to, sodium bisulfite and vitamin C. The preferred anti-oxidant is sodium bisulfite.

In addition, it is preferred that the galactose injection solutions contain galactose at a concentration of 4% to 40% by weight, the buffer solution at the concentration of 0.01 M to 1.0 M (most favorably at about 0.01 M), and the anti-oxidant at the concentration of 0.001% to 5% by weight (most favorably at 0.01 to 1% by weight).

DETAILED DESCRIPTION OF THE INVENTION

Figure 1:
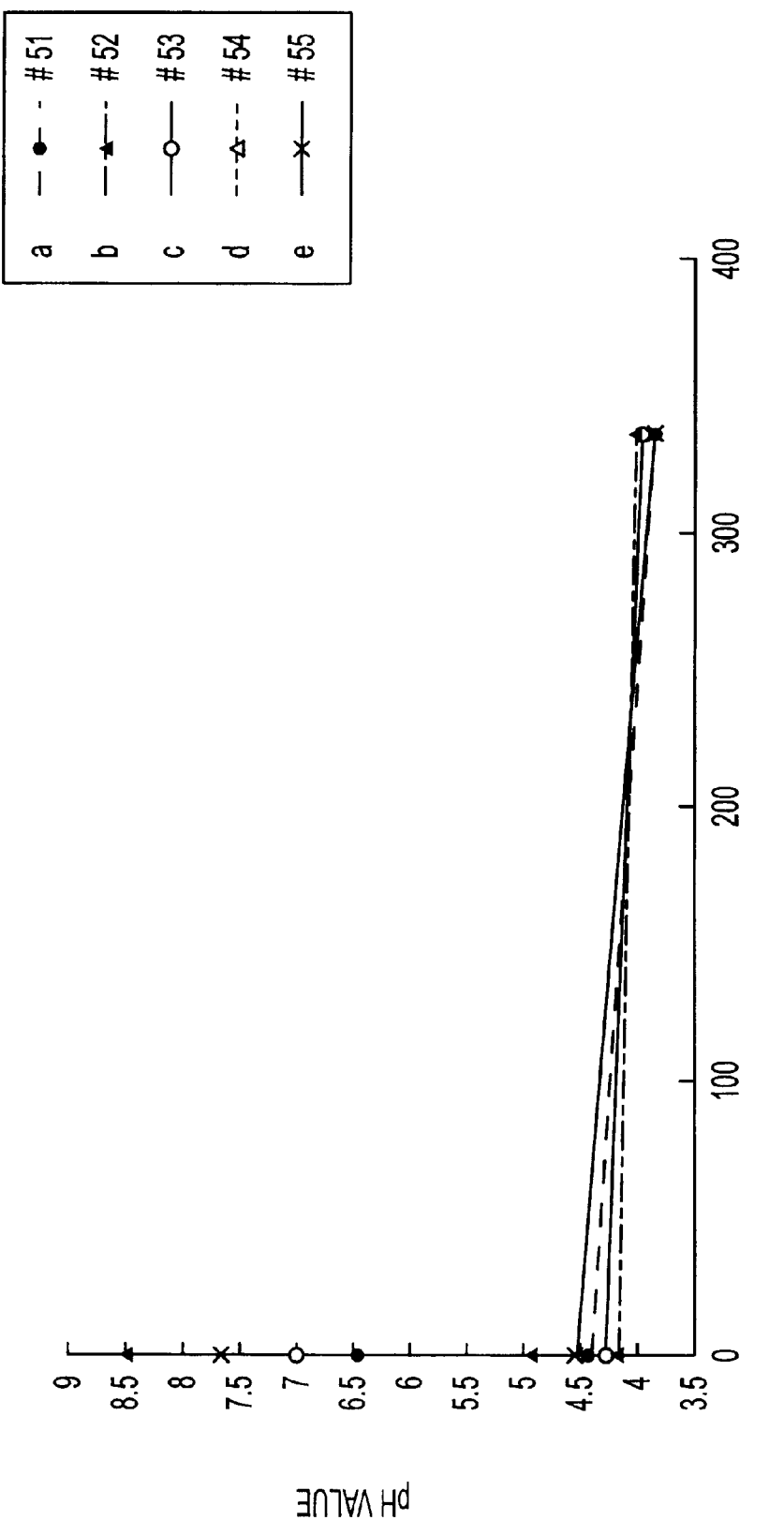
FIG. 1 shows the changes of pH over time for galactose injection solutions, which contain no anti-oxidant and no buffer solution. (a) Sample No. 51; (b) Sample No. 52; (c) Sample No. 53; (d) Sample No. 54; and (e) Sample No. 55.

The present invention provides formulations for galactose injection which have great stability. The stability of the formulations has been tested and determined by change of pH and color in the solution before and after sterilization by autoclaving and at high temperature for several weeks. The normal autoclaving time is about 15 minutes. The high temperature tested in the present invention is about 80° C. The tested period of time that the galactose injection solutions are stored at 80° C. is about two weeks.

The galactose injection solutions of the present invention are prepared by thoroughly mixing the galactose powder with the buffer solution and the anti-oxidant in a glass flask, preferably a Type I flask. A sample from the mixture is taken out for testing and the remaining mixture is sealed in the flask and placed in an autoclave to be sterilized at 121° C. (1.2 kg/cm$^2$) for about 15 minutes. A sample from the autoclaved flask is taken out for testing. The rest of the mixture is stored in an even at 80° C. for about 2 weeks. Each week, a sample is taken out from the flask for testing. The samples are tested on pH, light absorbance (OD at 284 nm wavelength), and galactose concentration, using conventional methods.

The galactose injection solutions, which contain galactose at various concentrations (1%–50% by weight), with or without a buffer solution, and with or without an anti-oxidant, are tested according to the following manner: For galactose, various dosages are chosen, which ranged between 4% and 40% by weight. For the buffer solution, 5 kinds of the buffer solution are chosen, which are citrate buffer, phosphate buffer, acetate buffer, carbonate buffer, and triethanolamine buffer. Within each buffer solution, various concentrations are tested, which ranged between 0.01 M to 1.0 M. For the anti-oxidant, two kinds of anti-oxidant are tested, which are sodium bisulfite (and/or metabisulfite) and vitamin C. Within each anti-oxidant, various concentrations are tested, which ranged between 0.001 and 5% by weight.

The samples were tested for stability on the basis of (1) color changes and any deposition; (2) change in pH value; and (3) change in light absorbance at $OD_{284}$ (which is based upon the conversion of dextrose to 5-hydroxymethylfurfural [HMF]); and (4) change in galactose concentration. The stability of the galactose injection solutions is tested based on the premises that the galactose was not degraded. It is known that galactose degradation produces 5-hydroxymethylfurfural (5-HMF), which gives rise to amber to yellow coloration.

The results of the above studies show that the most preferred galactose injection solution contains 0.4% or 4% of galactose with 0.01 M citrate buffer, and 0.5% sodium bisulfite, and at a pH of about 4.5.

The following examples are illustrative, and should not be viewed as limiting the scope of the present invention. Reasonable variations, such as those occur to reasonable artisan, can be made herein without departing from the scope of the present invention.

EXAMPLE 1
Preparation of Galactose Injection Solution Sample Nos. 1–10

Sample Nos. 1–10 represent galactose injection solutions containing 4% by weight of galactose (dissolved in distilled water), with no buffer, and with or without anti-oxidant. In the case when the anti-oxidant is contained in the galactose solution, two kinds of anti-oxidant (i.e., sodium bisulfite and vitamin C) in two different concentrations (i.e., 0.1% and 0.5% by weight) are tested. Sample Nos. 1–10 were prepared as follows:

1. Galactose powder (at the final concentration of 4% by weight) was weighed and thoroughly mixed in 100 ml of distilled water. For sample Nos. 1, and 3, 0.5% by weight of sodium bisulfite was added to the galactose mixture. For sample Nos. 2, and 4, 0.5% by weight of vitamin C was added to the galactose mixture. For sample Nos. 5, and 7, 0.1 % of sodium bisulfite was added to the galactose mixture. For sample Nos. 6, and 8, 0.1 % of vitamin C was added to the galactose mixture. For sample Nos. 9–10, no sodium bisulfite or vitamin C was added to the galactose mixture. Sample Nos. 1, 2, 5, 6, and 9, were adjusted to pH 7.35. Sample Nos. 3, 4, 7, 8, and 10 were adjusted to pH 4.5.

2. The galactose injection solutions of (1) were autoclaved at 121° C., 1.2kg/cm$^2$ for fifteen (15) minutes.

3. The galactose injection solutions of (2) were stored in an oven at 80° C. for 2 weeks.

Results

The results of sample Nos. 1–10 are described in Table 1.

TABLE 1

Composition of Galactose Injection Solution Sample Nos. 1–10.

| Formulation | 1 | 2 | 3 | 4 | 5 | 6 | 7 | 8 | 9 | 10 |
|---|---|---|---|---|---|---|---|---|---|---|
| Gal Conc. (%) | 4 | 4 | 4 | 4 | 4 | 4 | 4 | 4 | 4 | 4 |
| Water (ml) | 100 | 100 | 100 | 100 | 100 | 100 | 100 | 100 | 100 | 100 |
| pH | 7.35 | 7.35 | 4.5 | 4.5 | 7.35 | 7.35 | 4.5 | 4.5 | 7.35 | 4.5 |
| Antioxidant | Bisul. | Vit. C | Bisul. | Vit. C | Bisul. | Vit. C | Bisul. | Vit. C | | |
| (M) | 0.5 | 0.5 | 0.5 | 0.5 | 0.1 | 0.1 | 0.1 | 0.1 | | |
| color change after 1 week | ** | ***** | | **** | ** | *** | | *** | * | * |
| pH change after 2 weeks | 7.11 | 6.56 | 1.69 | 5.44 | 4.50 | 6.02 | 3.04 | 5.91 | 2.92 | 3.72 |
| conc. before sterilization (%) | | | | | | 2.082 | 2.853 | | | |
| conc. after sterilization (%) | | | | | | 2.216 | 2.549 | | | |
| conc. after 1 week (%) | | | | | | 2.365 | 2.430 | | | |
| conc. after 2 weeks (%) | | | | | | 1.620 | 2.252 | | | | gal = galactose; conc. = concentration; Bisul. = sodium bisulfite; Vit. C = vitamin C.
*represents the color of the solution, the more asterisk, the deeper the solution.

Sample Nos. 1–10 were 4% galactose injection solutions, which contained no buffer solution. As shown in Table 1, samples 9–10 represent galactose injection solutions without buffer solution and anti-oxidant. These two samples demonstrated minimal color change even after 2 weeks of incubation at 80° C. However, a substantial change in pH was observed in sample No. 9 (from pH 7.35 to pH 2.92), which was contrary to the moderate pH change in sample No. 10 (from pH 4.5 to pH 3.72).

When vitamin C was used as the anti-oxidant (sample Nos. 2, 4, 6, and 8), the galactose injection solutions changed color substantially after one (1) week at 80° C. This was contrary to sample Nos. 1, 3, 5 and 6, when sodium bisulfite was used as the antioxidant. Also, when the same amount of sodium bisulfite was used (i.e., sample No. 1 v. sample No. 3; sample No. 5 v. sample No. 7), the samples which had pH at 4.5 (i.e., sample Nos. 3 and 7) show the least color change after one (1) week at 80° C.

Furthermore, when sample No. 3 (0.5% sodium bisulfite) was compared with sample No. 7 (0.1 % sodium bisulfite), sample No. 7 was superior in terms of change in pH value (pH in sample No. 3 dropped from 4.5 to 1.69, while pH in sample No. 7 dropped from 4.5 to 3.04).

In conclusion, sample No. 7, which represents the galactose injection solution containing 0.1% sodium bisulfite (at pH 4.5), demonstrated the best stability among samples 1–10.

EXAMPLE 2

Preparation of Galactose Injection Solution Sample Nos. 11–30

Sample Nos. 11–30 represent galactose injection solutions containing 4% by weight of galactose, which were dissolved in a 0.01 M buffer solution, and further contained 0.1% by weight of sodium bisulfite or vitamin C. Five (5) kinds of buffer solution were tested, which were citrate buffer, phosphate buffer, acetate buffer, triethanolamine buffer, and carbonate buffer. Sample Nos. 11–30 were prepared as follows:

1. Galactose powder (at the final concentration of 4% by weight) was weighed and thoroughly mixed in a 0.01 M buffer solution. Five buffer groups (each contained 4 samples), which were based upon the kind of the buffer used in the galactose solution, were constructed as follows: (1) Citrate buffer group—Sample Nos. 11–14; (2) Phosphate buffer group—Sample Nos. 15–18; (3) Acetate buffer group—Sample No. 19–22; (4) Carbonate buffer group—Sample No. 23–26; and (5) Triethanolamine buffer group—Samples No. 27–20. Each buffer group was further subdivided into 2 pH subgroups, i.e., the first two samples of the buffer group were at pH 7.35 and the last two samples of the same buffer group were at pH 4.5. Also, within each pH subgroup, the first sample contained 0.1 % by weight of sodium bisulfite, and the second sample contained 0.1 % by weight of vitamin C.

2. The galactose injection solutions of (1) were autoclaved at 121 ° C., 1.2kg/cm$^2$ for fifteen (15) minutes.

3. The galactose injection solutions of (2) were stored in an oven at 80° C. for 2 weeks.

Results

The results of the stability studies in samples 11–30 are shown in Tables 2 and 3.

TABLE 2

Galactose Injection Solution Sample Nos. 11–20.

| Formulation | 11 | 12 | 13 | 14 | 15 | 16 | 17 | 18 | 19 | 20 |
|---|---|---|---|---|---|---|---|---|---|---|
| gal conc. % | 4 | 4 | 4 | 4 | 4 | 4 | 4 | 4 | 4 | 4 |
| Buffer | citr. | citr. | citr. | citr. | phos. | phos. | phos. | phos. | acet. | acet. |
| (M) | 0.01 | 0.01 | 0.01 | 0.01 | 0.01 | 0.01 | 0.01 | 0.01 | 0.01 | 0.01 |
| pH | 7.35 | 7.5 | 4.5 | 4.5 | 7.35 | 7.35 | 4.5 | 4.5 | 7.35 | 7.35 |
| antioxidant | bisul. | Vit. C | bisul. | Vit. C | bisul. | Vit. C | bisul. | Vit. C | bisul. | Vit. C |
| (M) | 0.1 | 0.1 | 0.1 | 0.1 | 0.1 | 0.1 | 0.1 | 0.1 | 0.1 | 0.1 |
| color change after 1 week | | *** | | **** | | ** | | ** | | ** |
| pH change after 2 weeks | 4.38 | 3.68 | 3.22 | 3.53 | 3.42 | 2.92 | 3.17 | 2.90 | 3.73 | 2.86 |
| precipitation | | | | + | | | | | | |
| conc. before steri. % | 2.788 | | 2.519 | | 2.498 | | 2.635 | | 2.198 | |
| conc. after steri. % | 2.221 | | 2.348 | | 2.305 | | 2.944 | | 2.377 | |
| conc. after 1 week % | 1.999 | | 2.641 | | 2.053 | | 2.233 | | 2.334 | |
| conc. after 2 weeks % | 2.341 | | 2.475 | | 1.947 | | 2.775 | | 3.164 | | gal = galactose; conc. = concentration; citr. = citrate buffer; phos. = phosphate buffer; acet. = acetate buffer; bisul. = sodium bisulfite; Vit. C = vitamin C; steri. = sterilization.
*indicates the color changes: the more asterisks, the deeper the color;
+ indicates precipitation.

TABLE 3

Galactose Injection Solution Samples Nos. 21–30.

| Formulation | 21 | 22 | 23 | 24 | 25 | 26 | 27 | 28 | 29 | 30 |
|---|---|---|---|---|---|---|---|---|---|---|
| gal conc. % | 4 | 4 | 4 | 4 | 4 | 4 | 4 | 4 | 4 | 4 |
| Buffer | acet. | acet. | carb. | carb. | carb. | carb. | TEA | TEA | TEA | TEA |
| (M) | 0.01 | 0.01 | 0.01 | 0.01 | 0.01 | 0.01 | 0.01 | 0.01 | 0.01 | 0.01 |
| pH | 4.5 | 4.5 | 7.35 | 7.35 | 4.5 | 4.5 | 7.35 | 7.35 | 4.5 | 4.5 |
| antioxidant | bisul. | Vit. C | bisul. | Vit. C | bisul. | Vit. C | bisul. | Vit. C | bisul. | Vit. C |
| (M) | 0.1 | 0.1 | 0.1 | 0.1 | 0.1 | 0.1 | 0.1 | 0.1 | 0.1 | 0.1 |
| color change after 1 week | | ** | | *** | | *** | | *** | | *** |

TABLE 3-continued

| | Galactose Injection Solution Samples Nos. 21–30. | | | | | | | | | |
|---|---|---|---|---|---|---|---|---|---|---|
| Formulation | 21 | 22 | 23 | 24 | 25 | 26 | 27 | 28 | 29 | 30 |
| pH change after 2 weeks | 3.54 | 2.67 | 4.00 | 3.08 | 2.94 | 2.54 | 3.38 | 2.62 | 3.12 | 2.44 |
| precipitation | | | | | | + | | | | |
| conc. before steri. % | 2.502 | | 2.436 | | 3.128 | | 2.671 | | 2.212 | |
| conc. after ster. % | 2.693 | | 2.848 | | 3.027 | | 3.134 | | 2.970 | |
| conc. after 1 week % | 2.019 | | 2.533 | | 2.610 | | 2.537 | | 2.595 | |
| conc. after 2 weeks % | 3.012 | | 2.640 | | 2.716 | | 2.633 | | 2.781 | | gal = galactose; conc. = concentration; acet. = acetate buffer; carb. = carbonate buffer; TEA = triethanolamine buffer; bisul. = sodium bisulfite; Vit. C = vitamin C; ster. = sterilization.
*indicates the color changes: the more asterisks, the deeper the color;
+ indicates precipitation.

As shown in Tables 2 and 3, samples containing vitamin C (i.e., samples Nos. 12, 14, 16, 18, 20, 22, 24, 26, 28, 30) all showed color changes one week after storage at 80° C.; which were contrary to samples containing sodium bisulfite (i.e., samples Nos. 11, 13, 15, 17, 19, 21, 23, 25, 27, 29), which demonstrated no color change at the same condition. Samples 14 and 26 developed precipitants after 2 weeks at 80° C.

Among the samples containing sodium bisulfite, pH did not appear to play a significant role in controlling the change in color. However, the samples at pH 4.5 appeared to demonstrate less change in pH than those at pH 7.35.

There appeared to be no difference in terms of preserving galactose stability among the kinds of buffer used in Samples 11–20. Thus, in conclusion, for 4% galactose injection solution in any of the five 0.01 M buffer solutions, 0.1% by weight of sodium bisulfite appeared to be better in stability than 0.1% by weight of vitamin C, and the galactose solution at pH 4.5 appeared to be better in stability than that at pH 7.35.

EXAMPLE 3

Preparation of Galactose Injection Solution Sample Nos. 31 . 50

Sample Nos. 31–50 represent galactose injection solutions containing 4% by weight of galactose, which were dissolved in a 1 M buffer solution, and further contain 0.5% by weight of sodium bisulfite or vitamin C. Five (5) kinds of buffer solution were tested, which were citrate buffer, phosphate buffer, acetate buffer, triethanolamine buffer, and carbonate buffer. Sample Nos. 31–50 were prepared as follows:

1. Galactose powder (at the final concentration of 4% by weight) was weighed and thoroughly mixed in a 1 M buffer solution. Five buffer groups (each contained 4 samples), which were based upon the kind of the buffer used in the galactose solution, were constructed as follows: (1) Citrate buffer group—Sample Nos. 31–34; (2) Phosphate buffer group—Sample Nos. 35–38; (3) Acetate buffer group—Sample No. 39–42; (4) Carbonate buffer group—Sample No. 43–46; and (5) Triethanolamine buffer group—Samples No. 47–50. Each buffer group was further subdivided into 2 pH subgroups, i.e., the first two samples of the buffer group were at pH 7.35 and the last two samples of the same buffer group were at pH 4.5. Also, within each pH subgroup, the first sample contained 0.5% by weight of sodium bisulfite, and the second sample contained 0.5% by weight of vitamin C.

2. The galactose injection solutions of (1) were autoclaved at 121° C., 1.2kg/cm$^2$ for fifteen (15) minutes.

3. The galactose injection solutions of (2) were stored in an oven at 80° C. for 2 weeks.

Results

The results of the stability studies of samples Nos. 31–50 are described in Tables 4–5.

| | Galactose Injection Solution Sample Nos. 31–40. | | | | | | | | | |
|---|---|---|---|---|---|---|---|---|---|---|
| Formulation | 31 | 32 | 33 | 34 | 35 | 36 | 37 | 38 | 39 | 40 |
| gal conc. % | 4 | 4 | 4 | 4 | 4 | 4 | 4 | 4 | 4 | 4 |
| Buffer | citr. | citr. | citr. | citr. | phos. | phos. | phos. | phos. | acet. | acet. |
| (M) | 1 | 1 | 1 | 1 | 1 | 1 | 1 | 1 | 1 | 1 |
| pH | 7.35 | 7.35 | 4.5 | 4.5 | 7.35 | 7.35 | 4.5 | 4.5 | 7.35 | 7.35 |
| antioxidant | bisul. | Vit. C | bisul. | Vit. C | bisul. | Vit. C | bisul. | Vit. C | bisul. | Vit. C |
| (M) | 0.5 | 0.5 | 0.5 | 0.5 | 0.5 | 0.5 | 0.5 | 0.5 | 0.5 | 0.5 |
| color change after 1 week | * | ***** | | ***** | * | ***** | | ***** | | **** |
| pH change after 2 weeks | 5.84 | 5.48 | 4.48 | 4.41 | 6.15 | 5.70 | 3.76 | 3.50 | 5.54 | 5.23 |
| precipitation | | | | | | | | | | + |

-continued

Galactose Injection Solution Sample Nos. 31–40.

| Formulation | 31 | 32 | 33 | 34 | 35 | 36 | 37 | 38 | 39 | 40 |
|---|---|---|---|---|---|---|---|---|---|---|
| conc. before steri. % | | | 2.476 | | | | 2.427 | | 2.410 | |
| conc. after steri. % | | | 1.392 | | | | 2.190 | | 1.716 | |
| conc. after 1 week % | | | 1.208 | | | | 2.177 | | 1.471 | |
| conc. after 2 weeks % | | | 0.700 | | | | 1.873 | | 0.798 | | gal = galactose; conc. = concentration; citr. = citrate buffer; phos. = phosphate buffer; acet. = acetate buffer; bisul. = sodium bisulfite; Vit. C = vitamin C; steri. = sterilization.
*indicates the color changes: the more asterisks, the deeper the color;
+ indicates precipitation.

TABLE 5

Galactose Injection Solution Sample No. 41–50.

| Formulation | 41 | 42 | 43 | 44 | 45 | 46 | 47 | 48 | 49 | 50 |
|---|---|---|---|---|---|---|---|---|---|---|
| gal conc. % | 4 | 4 | 4 | 4 | 4 | 4 | 4 | 4 | 4 | 4 |
| Buffer | acet. | acet. | carb. | carb. | carb. | carb. | TEA | TEA | TEA | TEA |
| (M) | 1 | 1 | 1 | 1 | 1 | 1 | 1 | 1 | 1 | 1 |
| pH | 4.5 | 4.5 | 7.35 | 7.35 | 4.5 | 4.5 | 7.35 | 7.35 | 4.5 | 4.5 |
| antioxidant | bisul. | Vit. C | bisul. | Vit. C | bisul. | Vit. C | bisul. | Vit. C | bisul. | Vit. C |
| (M) | 0.5 | 0.5 | 0.5 | 0.5 | 0.5 | 0.5 | 0.5 | 0.5 | 0.5 | 0.5 |
| color change after 1 week | | ***** | ** | ***** | | ***** | | **** | * | ***** |
| pH change after 2 weeks | 4.32 | 4.11 | 6.94 | 6.74 | 4.84 | 1.78 | 5.97 | 4.28 | 1.68 | 1.78 |
| precipitation | | + | | | | + | | | | + |
| conc. before steri. % | 3.013 | | | | 2.501 | | 2.279 | | | |
| conc. after steri. % | 2.677 | | | | 2.089 | | 1.962 | | | |
| conc. after 1 week % | 2.061 | | | | 1.604 | | 1.152 | | | |
| conc. after 2 weeks % | 1.992 | | | | 0.926 | | 0.653 | | | | gal = galactose; conc. = concentration; acet. = acetate buffer; carb. = carbonate buffer; TEA = triethanolamine buffer; bisul. = sodium bisulfite; Vit. C = vitamin C; steri. = sterilization.
*indicates the color changes: the more asterisks, the deeper the color;
+ indicates precipitation.

As shown in Tables 4 and 5, samples containing vitamin C (i.e., samples Nos. 32, 34, 36, 38, 40, 42, 44, 46, 48, 50) all showed color changes one week after storage at 80° C. In samples containing sodium bisulfite (i.e., samples Nos. 31, 33, 35, 37, 39, 41, 43, 45, 47, 49), samples Nos. 31, 35, 43, and 49 showed a moderate change in color after being stored at 80° C. for 1 week. In addition, galactose solution in 1 M carbonate buffer (pH 7.35) or in 1 M triethanolamine buffer (pH 4.5) both demonstrated color change after being stored at 80° C. for 1 week. Furthermore, samples Nos. 31–50 demonstrated higher galactose degradation (as determined by the change in galactose concentration after being stored at 80° C. for 2 weeks) than samples Nos. 1–30.

Thus, the results of stability studies in Tables 4 and 5 suggest that the galactose solution with a buffer solution in higher concentration (0.01 M vs. 1 M), and/or an anti-oxidant in higher concentration (0.1% vs. 0.5%) was less stable than those in lower concentration. Among the buffer solutions tested in Tables 4 and 5, citrate buffer and acetate buffer appeared to produce more stable result than phosphate buffer, carbonate buffer, and triethanolamine buffer. Finally, when higher concentration of the buffer solution and higher concentration of the anti-oxidant were used, lower pH provided better stability than higher pH (e.g., galactose injection solutions at pH 4.5 demonstrated better stability than those at pH 7.35).

EXAMPLE 4

Preparation of Galactose Injection Solution Sample Nos. 51–61

Sample Nos. 50–55 represent galactose injection solutions containing 4% by weight of galactose, with no buffer solution and anti-oxidant. These samples were conducted to determine the effect of pH on stability of the galactose injection solutions.

Sample Nos. 56–61 represent galactose injection solutions containing 4% by weight of galactose, no buffer solution, and three different concentrations (i.e., 0.01%, 0.1% and 1% by weight) of bisulfite (samples Nos. 56–58) and metabisulfite (samples Nos. 59–61). This set of samples was conducted to determine the effect of anti-oxidant concentrations on stability of the galactose injection solutions. Sample Nos. 51–61 were prepared as follows:

1.
For sample Nos. 51–55, in each sample, galactose powder (at the final concentration of 4% by weight) was weighed and thoroughly mixed in 100 ml of distilled water. Each of the galactose injection solution was adjusted to pH ranged between 5.02 and 8.52 (sample No. 51: pH 6,44; sample No. 52: pH 5.02, sample No. 53: pH 7.01; sample No. 54: pH 8.52; sample No. 55: pH 7.69).

For sample Nos. 56–61, in each sample, galactose powder (at the final concentration of 4% by weight) was weighed and thoroughly mixed in 100 ml of distilled water. In sample Nos. 56–58, 0.01% (No. 56), 0.1% (No. 57), and 1% (No. 58) by weight of bisulfite was added to each of the galactose injection solutions. In sample Nos. 59–61, 0.01% (No. 59), 0.1 % (No. 60), and 1% (No. 61) by weight of metabisulfite was added to each of the galactose injection solutions.

2. Each of the galactose injection solutions described in (1) was autoclaved at 121° C., 1.2kg/cm$^2$ for fifteen (15) minutes.
3. Each of the galactose injection solutions described in (2) was stored in an oven at 80° C. for 2 weeks.

Results

Figure 2:
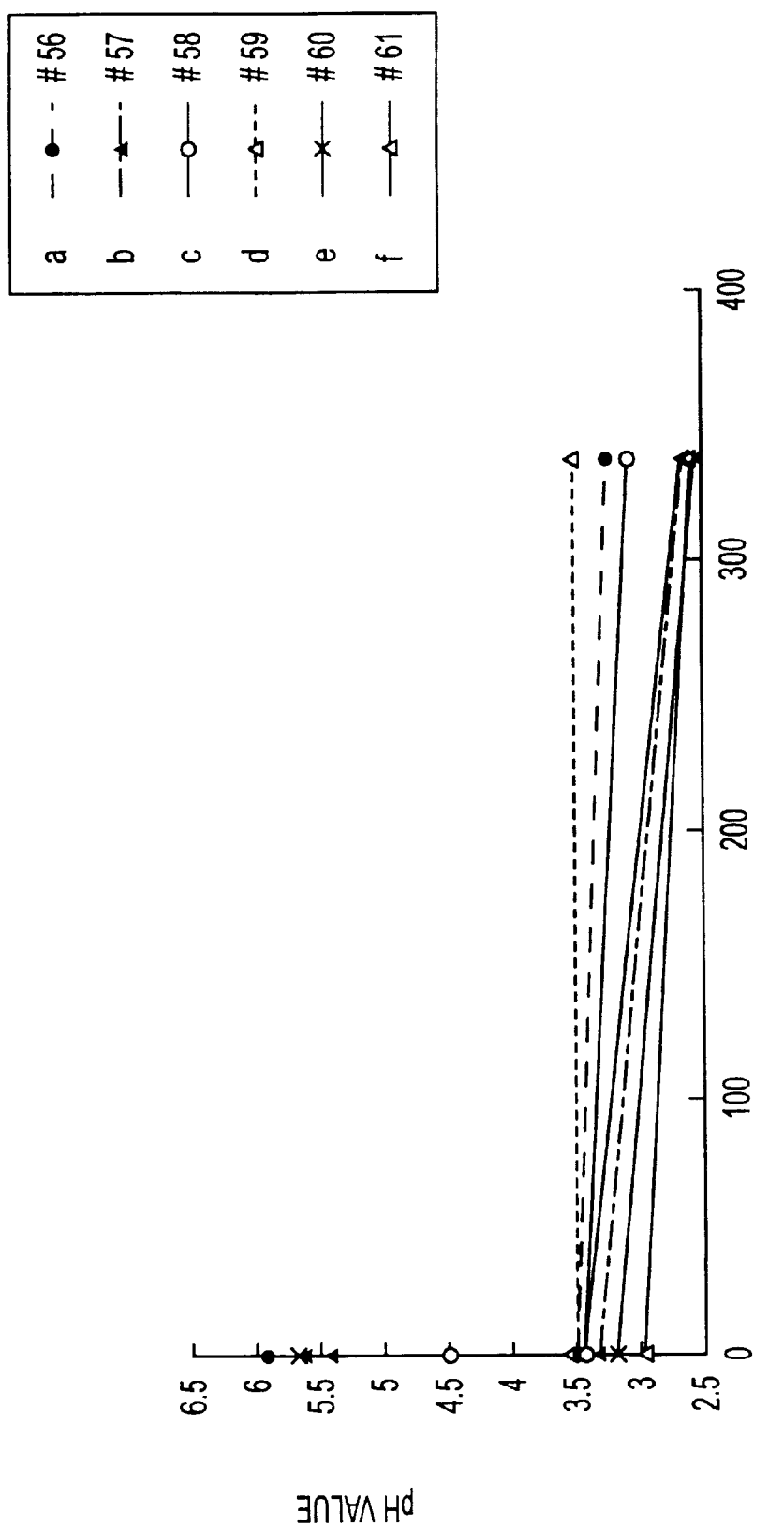
FIG. 2 shows the changes of pH over time for galactose injection solutions, which contain anti-oxidant but are without buffer solution. (a) Sample No. 56; (b) Sample No. 57; (c) Sample No. 58; (d) Sample No. 59; and (e) Sample No. 60.

The results of the stability studies of samples Nos. 51–61 are described in Tables 6–7 and FIGS. 1 and 2.

TABLE 6

Galactose Injection Solution Nos. 51–55.

| Formulation | 51 | 52 | 53 | 54 | 55 |
|---|---|---|---|---|---|
| gal conc. % | 4 | 4 | 4 | 4 | 4 |
| Buffer (M) | | | | | |
| antioxidant (M) | | | | | |
| pH before sterilization | 6.44 | 5.02 | 7.01 | 8.52 | 7.69 |
| pH after sterilization | 3.86 | 4.5 | 3.98 | 3.98 | 3.89 |
| color change after 2 weeks | ** | * | ** | ** | ** |
| O.D. before sterilization | 0.022 | 0.027 | 0.016 | 0.030 | 0.024 |
| O.D. after sterilization | 0.040 | 0.039 | 0.034 | 0.050 | 0.036 |
| O.D. in the first week | 0.065 | 0.346 | 0.386 | 0.452 | 0.450 |
| O.D. in the second week | 1.107 | 0.624 | 0.719 | 0.827 | 1.157 |
| conc. before sterilization | | | | | |
| conc. after sterilization | | | | | |
| conc. in the first week | | | | | |
| conc. in the second week | | | | | |
| reason for rejection | color | color | color | color | color | gal = galactose; conc. = concentration; steri. = sterilization.
*indicates the color changes: the more asterisks, the deeper the color.

TABLE 7

Galactose Injection Solution Nos. 56–61.

| Formulation | 56 | 57 | 58 | 59 | 60 | 61 |
|---|---|---|---|---|---|---|
| gal conc. % | 4 | 4 | 4 | 4 | 4 | 4 |
| Buffer (M) | | | | | | |
| antioxidant (%) | bisulfite 0.01 | bisulfite 0.1 | bisulfite 1 | metabisulfite 0.01 | metabisulfite 0.1 | metabisulfite 1 |
| pH before sterilization | 5.93 | 5.45 | 4.48 | 5.65 | 5.67 | 4.53 |
| pH after sterilization | 3.20 | 2.63 | 3.04 | 3.49 | 2.52 | 2.57 |
| color change after 2 weeks | * | | | * | | |
| O.D. before sterilization | 0.013 | 0.007 | 0.020 | 0.019 | 0.006 | 0.023 |
| O.D. after sterilization | 0.046 | 0.019 | 0.039 | 0.058 | 0.024 | 0.132 |
| O.D. in the first week | 0.355 | 0.110 | 0.104 | 0.362 | 0.128 | 0.227 |
| O.D. in the second week | 0.612 | 0.207 | 0.107 | 0.566 | 0.347 | 0.198 |
| conc. before sterilization | | 100 | 100 | | 100 | 100 |
| conc. after sterilization | | 80.8 | 88.5 | | 88.7 | 112.1 |
| conc. in the first week | | 112.2 | 69.1 | | 93.9 | 90.9 |
| conc. in the second week | | 97.7 | 83.1 | | 98.0 | 59.0 |
| reason for rejection | color | pH | pH | color | pH | pH | gal = galactose; conc. = concentration; steri. = sterilization.
*indicates the color changes: the more asterisks, the deeper the color.

The results, as shown in Table 6 and FIG. 1, demonstrate that the galactose injection solution at lower pH displaced less change in pH after autoclaving, particularly as evidenced by the finding in sample No. 52, which had the lowest pH (i.e., pH at 5.02) and also the least change in pH, the least change in color, and the least change in light absorbance at 284 nm.

In accordance with the USP XXII standard, the major metabolite for dextrose injection formulation is 5-hydroxymethyl-furfural (5-HMF) and/or its related compounds. Under this standard, the acceptable galactose solution for injection should be no more than a change in the relative light absorbance of 0.25 (at 284 nm) when dextrose concentration in the formulation was 1/250 g/ml (i.e., 0.4%), using water as blank, to guarantee the occurrence of the least dextrose degradation. Correspondingly, the change in the relative light absorbance in the 4% galactose solution should be no more than 2.5 to qualify the galactose solution to be used for injection. Accordingly, sample No. 52 was qualified to be a galactose injection solution after autoclaving due to its showing of the least change in pH and in light absorbance.

The results, as shown in Table 7 and FIG. 2, demonstrate that the addition of anti-oxidant (either bisulfite or metabisulfite) to the galactose injection solution improves the stability of the galactose injection solution, both in preserving the color, and in reducing change in pH value and light absorbance at 284 nm. Within the tested concentration range (i.e., 0.01% to 1% by weight), 1% of either bisulfite or metabisulfite appeared to provide better stability.

EXAMPLE 5

Preparation of Galactose Injection Solution Sample Nos. 62–75

Sample Nos. 62–75 represents galactose injection solutions containing 4% by weight of galactose, with 0.01% or 1% by weight of sodium bisulfite, and with (1) 0.01 M citrate buffer (sample Nos. 62–65), (2) 0.01 M phosphate buffer (sample Nos. 66–69), (3) 0.01 M acetate buffer (sample Nos. 70–73), and (4) 0.01 M triethanolamine buffer (sample Nos. 74–75).

Sample Nos. 62–75 were prepared as follows:

1. Samples Nos. 62–75 were subdivided into 4 groups based on the kind of buffer solutions (i.e., citrate buffer, phosphate buffer, acetate buffer, and triethanolamine buffer) used in the study. All buffer solutions were set at 0.01 M. In each sample, galactose powder (at the final concentration of 4% by weight) was weighed and thoroughly mixed with the designated buffer solution. Within each group, two different concentrations (0.01% or 1%) of sodium bisulfite were added in accordance with the experimental design as shown in Tables 8–10. Each sample also was adjusted to different pH in accordance with the experimental design (Tables 8–10).
2. Each of the galactose injection solutions described in (1) was autoclaved at 121° C., 1.2kg/cm² for fifteen (15) minutes.
3. Each of the galactose injection solutions described in (2) was stored in an oven at 80° C. for 2 weeks.

Results

The results of the stability studies for sample Nos. 62–75 are shown in Tables 8–10 and FIGS. 3–6.

TABLE 8

Galactose Injection Solution Nos. 62–65.

| Formulation | 62 | 63 | 64 | 65 |
|---|---|---|---|---|
| galactose concentration % | 4 | 4 | 4 | 4 |
| Buffer | citrate | citrate | citrate | citrate |
| (M) | 0.01 | 0.01 | 0.01 | 0.01 |
| antioxidant (%) | bisulfite 0.01 | bisulfite 1 | bisulfite 0.01 | bisulfite 1 |
| pH before sterilization | 7.38 | 6.09 | 4.47 | 4.32 |
| pH after sterilization | 4.86 | 4.64 | 3.59 | 3.58 |
| color change after 2 weeks | *** | | | |
| O.D. before sterilization | 0.017 | 0.017 | 0.013 | 0.026 |
| O.D. after sterilization | 0.660 | 0.114 | 0.023 | 0.017 |
| O.D. in the first week | 1.710 | 0.288 | 0.136 | 0.036 |
| O.D. in the second week | 2.501 | 0.290 | 2.282 | 0.060 |
| conc. before sterilization | | 100 | 100 | 100 |
| conc. after sterilization | | 80.9 | 71.1 | 76.0 |
| conc. in the first week | | 79.4 | 82.1 | 93.7 |
| conc. in the second week | | 67.5 | 74.0 | 73.9 |
| reason for rejection | color | concentration | | light absorbance | conc. = concentration;
*indicates the color changes: the more asterisks, the deeper the color.

Sample Nos. 62–65 contained 4% galactose, 0.01 M citrate buffer, and 0.01% by weight of bisulfite (sample Nos. 62 and 64), or 1% by weight of bisulfite (sample Nos. 63 and 65). In addition, sample No. 62 had a pH of 7.38, sample No. 63 had a pH of 6.09, sample No. 64 had a pH of 4.47 and sample No. 65 had a pH of 4.32.

Figure 3:
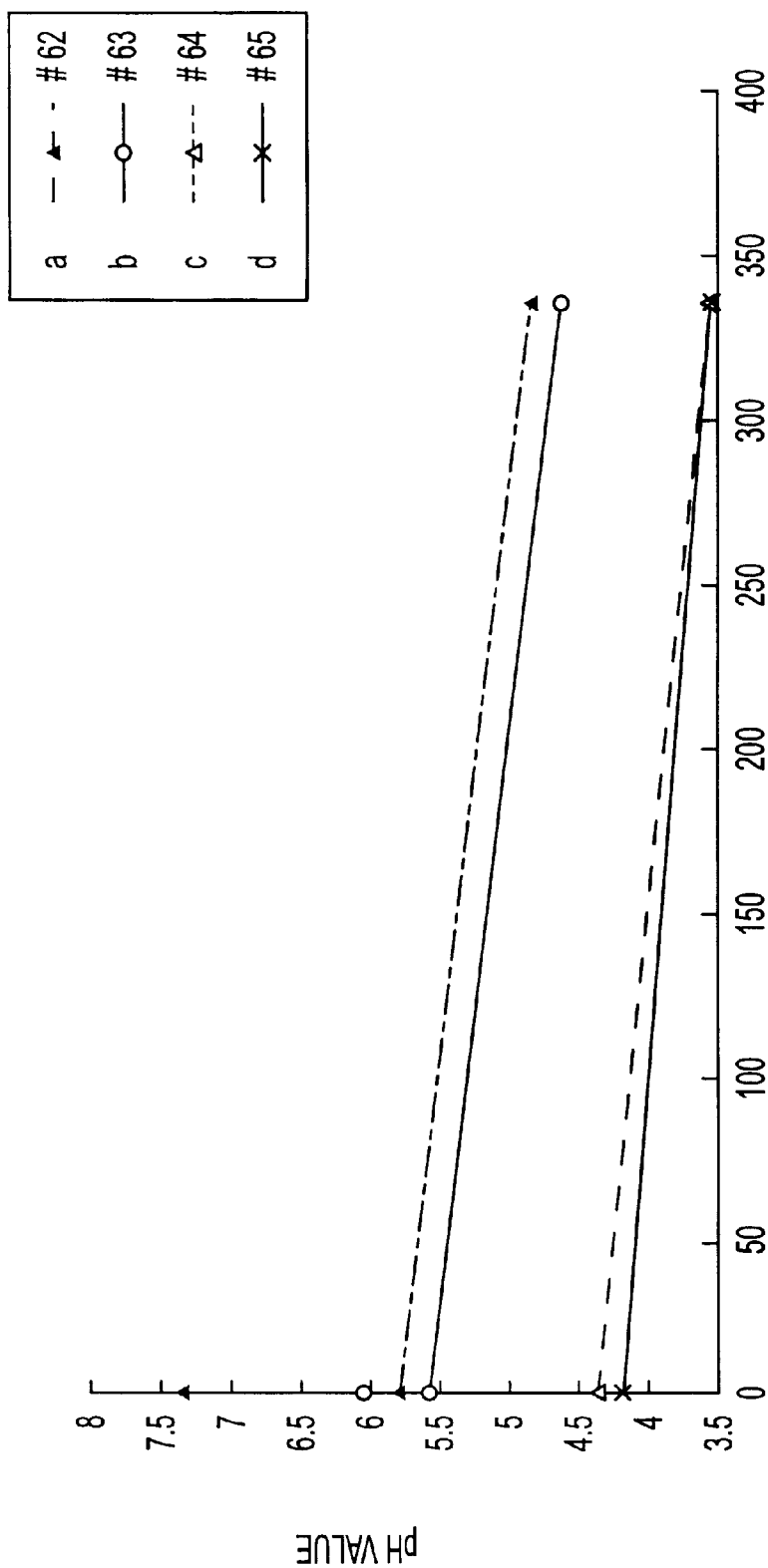
FIG. 3 shows the changes of pH over time for galactose injection solutions, which contain 0.01 M citrate buffer and different concentrations of sodium bisulfite. (a) Sample No. 62; (b) Sample No. 63; (c) Sample No. 64; and (d) Sample No. 65.

As demonstrated in Table 8 and FIG. 3, sample No. 65 appeared to be the most stable sample, in terms of the least change in color, in pH value, and in light absorbance. This result suggests that 1% bisulfite and acidic pH contribute to the stability of the galactose injection solution.

TABLE 9

Galactose Injection Solution Nos. 66–69.

| Formulation | 66 | 67 | 68 | 69 |
|---|---|---|---|---|
| galactose concentration % | 4 | 4 | 4 | 4 |
| Buffer | phosphate | phosphate | phosphate | phosphate |
| (M) | 0.01 | 0.01 | 0.01 | 0.01 |
| antioxidant (%) | bisulfite 0.01 | bisulfite 1 | bisulfite 0.01 | bisulfite 1 |
| pH before sterilization | 7.19 | 5.85 | 4.36 | 4.45 |
| pH after sterilization | 4.16 | 3.59 | 3.42 | 3.06 |
| color change after 2 weeks | *** | | * | |
| O.D. before sterilization | 0.024 | 0.021 | 0.014 | 0.014 |
| O.D. after sterilization | 0.745 | 0.146 | 0.058 | 0.026 |
| O.D. in the first week | 2.366 | 0.195 | 0.344 | 0.086 |
| O.D. in the second week | 2.501 | 0.234 | 0.604 | 0.092 |
| conc. before sterilization | | 100 | | 100 |
| conc. after sterilization | | 116.9 | | 108.4 |

TABLE 9-continued

Galactose Injection Solution Nos. 66–69.

| Formulation | 66 | 67 | 68 | 69 |
|---|---|---|---|---|
| conc. in the first week | | 131.9 | | 97.5 |
| conc. in the second week | | 102.1 | | 157.2 |
| reason for rejection | color | pH | color | | conc. = concentration;
* indicates the color changes: the more asterisks, the deeper the color.

Sample Nos. 66–69 contained 4% galactose, 0.01 M phosphate buffer, and 0.01% by weight of bisulfite (sample Nos. 66 and 68), or 1% by weight of bisulfite (sample Nos. 67 and 69). In addition, sample No. 66 had a pH of 7.19, sample No. 67 had a pH of 5.85, sample No. 68 had a pH of 4.36 and sample No. 69 had a pH of 4.45.

Figure 4:
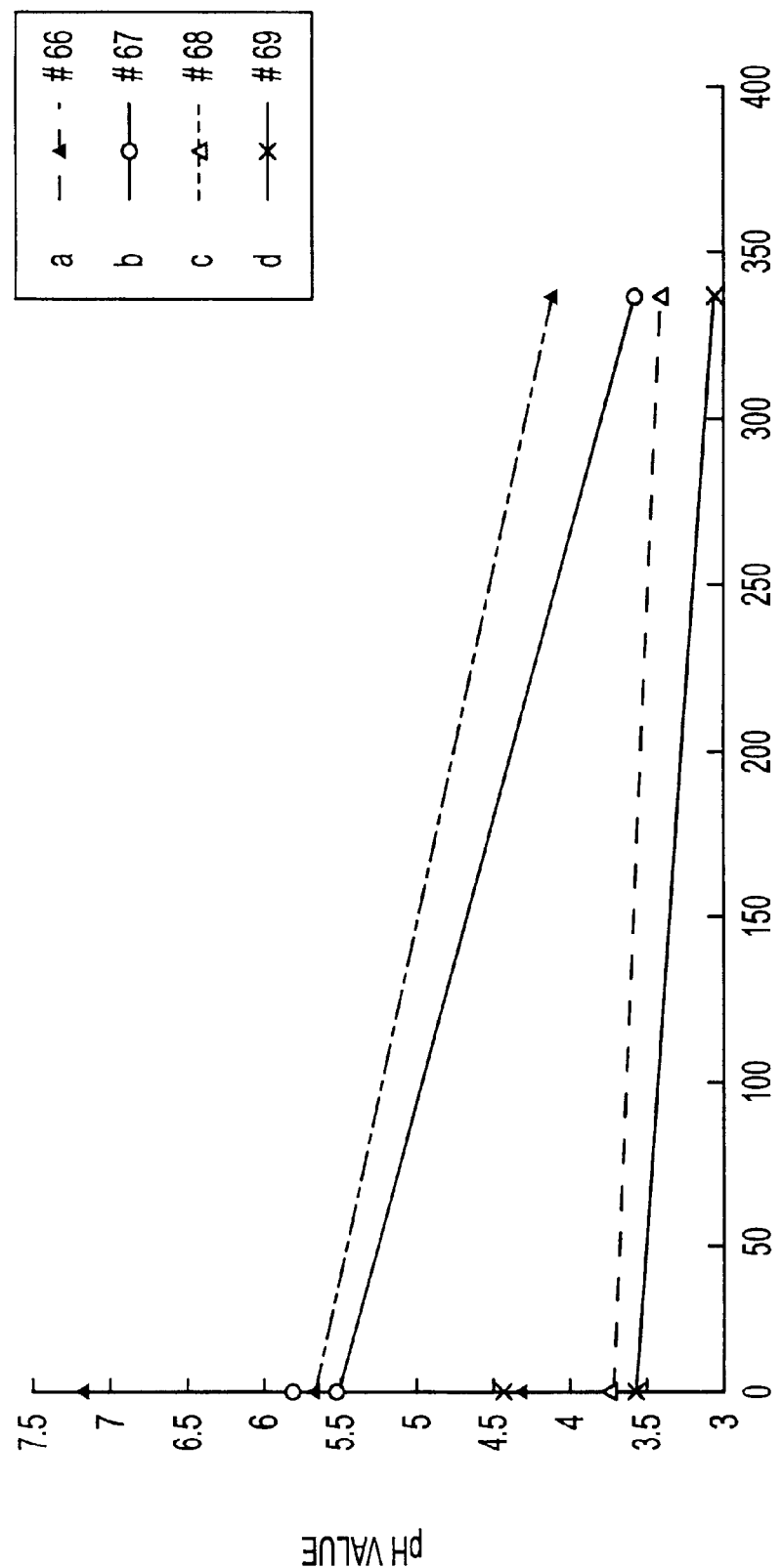
FIG. 4 shows the changes of pH over time for galactose injection solutions, which contain 0.01 M citrate buffer, and different concentrations of sodium bisulfite. (a) Sample No. 66; (b) Sample No. 67; (c) Sample No. 68; and (d) Sample No. 69.

As demonstrated in Table 9 and FIG. 4, sample No. 69 appeared to be the most stable sample, in terms of the least change in color, in pH value, and in light absorbance. This result suggests that 1% bisulfite and acidic pH contribute to the stability of the galactose injection solution.

TABLE 10

Galactose Injection Solution Nos. 70–75.

| Formulation | 70 | 71 | 72 | 73 | 74 | 75 |
|---|---|---|---|---|---|---|
| galactose concentration % | 4 | 4 | 4 | 4 | 4 | 4 |
| Buffer | acetate | acetate | acetate | acetate | TEA | TEA |
| (M) | 0.01 | 0.01 | 0.01 | 0.01 | 0.01 | 0.01 |
| antioxidant | bisulfite | bisulfite | bisulfite | bisulfite | bisulfite | bisulfite |
| (%) | 0.01 | 1 | 0.01 | 1 | 0.01 | 1 |
| pH before sterilization | 6.45 | 5.40 | 4.32 | 4.35 | 7.42 | 5.58 |
| pH after sterilization | 4.77 | 3.64 | 3.90 | 3.14 | 4.22 | 3.28 |
| color change after 2 weeks | *** | | ** | | *** | |
| O.D. before sterilization | 0.015 | 0.011 | 0.014 | 0.017 | 0.013 | 0.013 |
| O.D. after sterilization | 0.066 | 0.018 | 0.052 | 0.021 | 0.038 | 0.26 |
| O.D. in the first week | 0.357 | 0.029 | 0.289 | 0.065 | 0.491 | 0.050 |
| O.D. in the second week | 0.840 | 0.047 | 0.544 | 0.083 | 1.707 | 0.072 |
| conc. before sterilization | | 100 | | 100 | | 100 |
| conc. after sterilization | | 73.3 | | 96.5 | | 93.7 |
| conc. in the first week | | 78.6 | | 87.7 | | 85.0 |
| conc. in the second week | | 86.4 | | 89.0 | | 87.8 |
| reason for rejection | color | pH | color | | color | pH | conc. = concentration; TEA = triethanolamine buffer;
*indicates the color changes: the more asterisks, the deeper the color.

Table 10 includes two groups of studies. The first group, which includes sample Nos. 70–73, contained 4% galactose, 0.01 M acetate buffer and 0.01% by weight of bisulfite (sample Nos. 70 and 72), or 1% by weight of bisulfite (sample Nos. 67 and 69). In addition, sample No. 70 had a pH of 6.45, sample No. 71 had a pH of 5.40, sample No. 72 had a pH of 4.32 and sample No. 72 had a pH of 4.35.

The second group, which includes sample Nos. 74 and 75, contained 4% galactose, 0.01 M triethanolamine buffer and 0.01% by weight of bisulfite (sample No. 74), or 1% by weight of bisulfite (sample No. 75). In addition, sample No. 74 had a pH of 7.42, sample No. 75 had a pH of 5.58.

Figure 5:
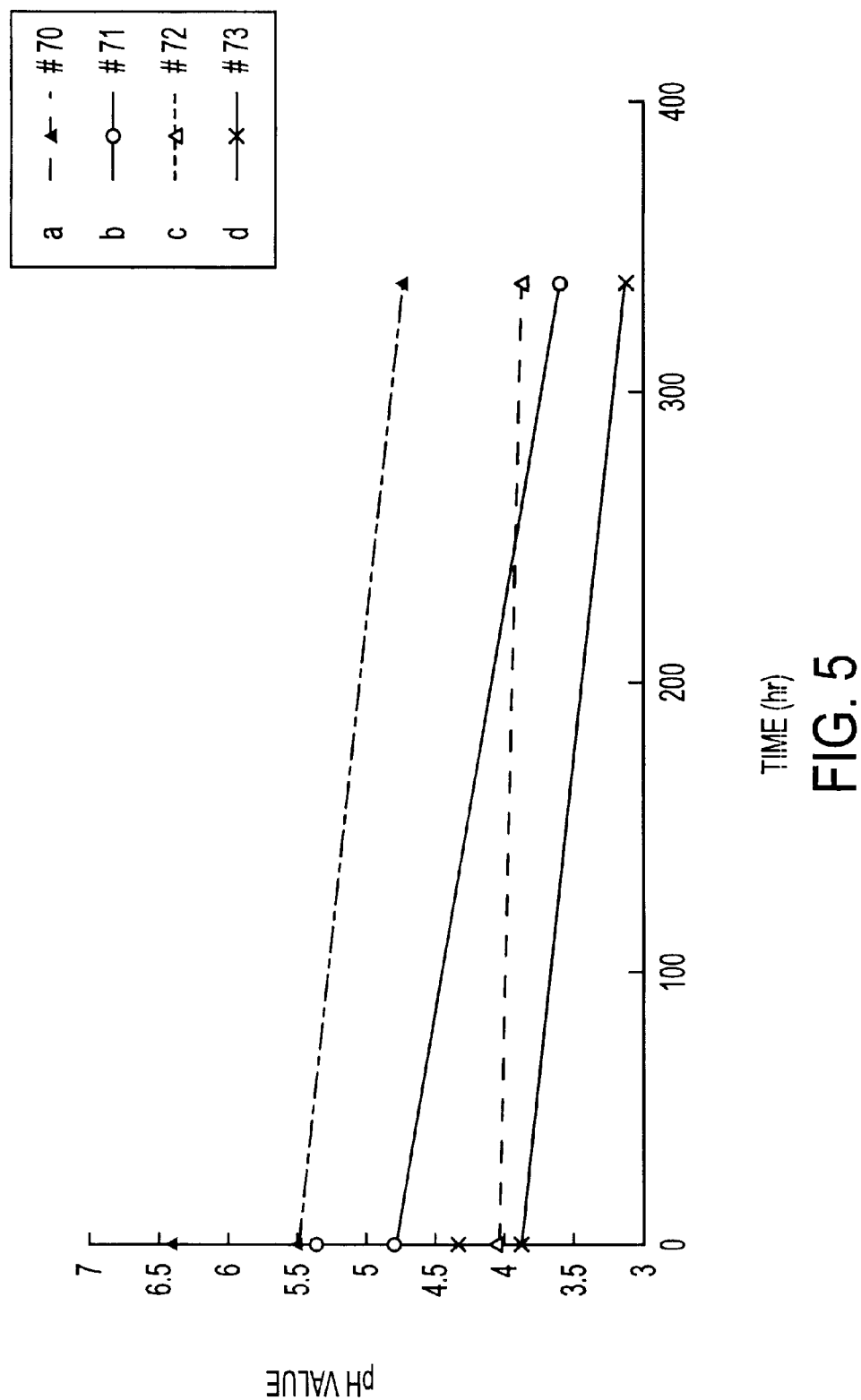
FIG. 5 shows the changes of pH over time for galactose injection solutions, which contain 0.01 M citrate buffer, and different concentrations of sodium bisulfite. (a) Sample No. 70; (b) Sample No. 71; (c) Sample No. 72; and (d) Sample No. 73.
Figure 6:
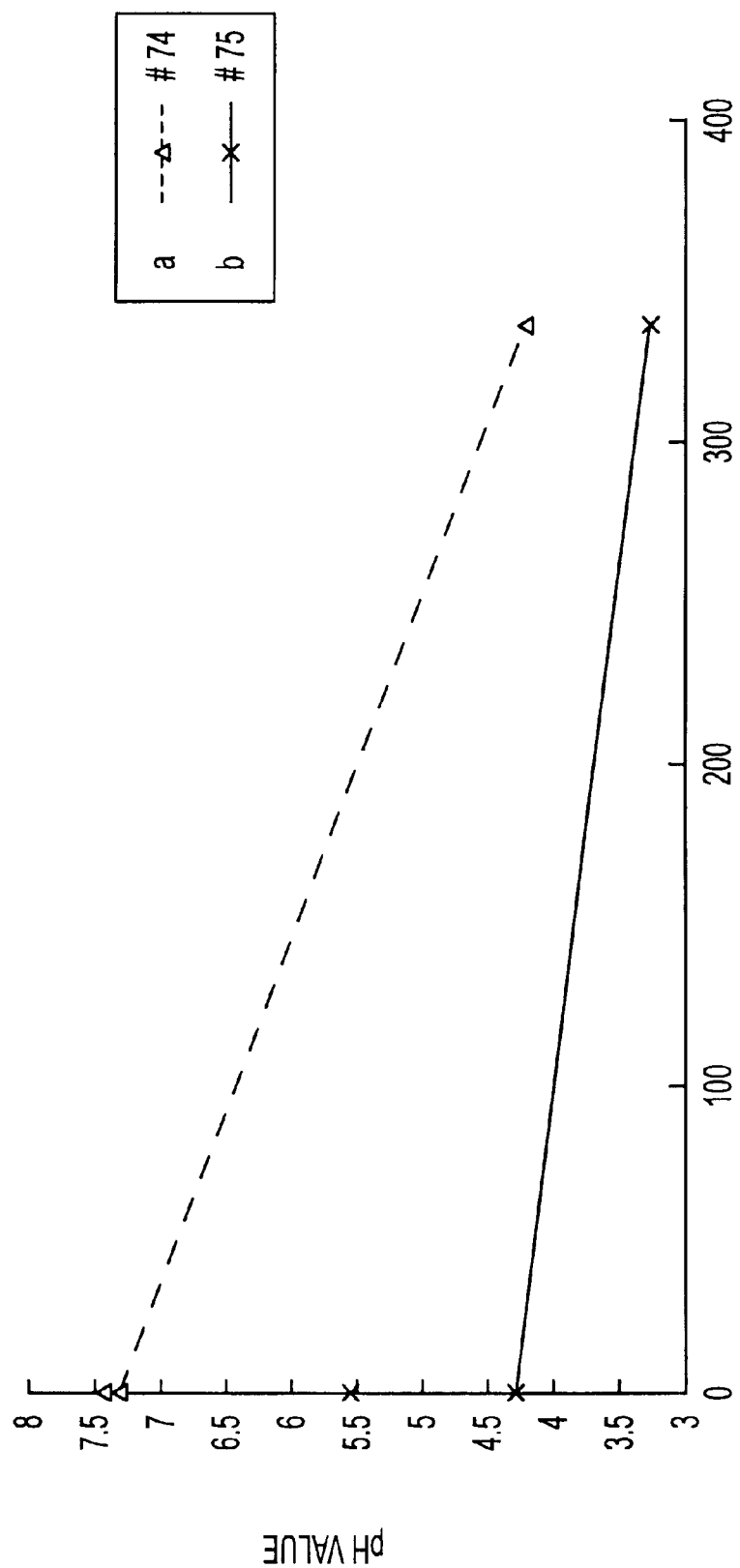
FIG. 6 shows the changes of pH over time for galactose injection solutions, which contain triethanolamine and different concentrations of sodium bisulfite. (a) Sample No. 74; and (b) Sample No. 75.

As demonstrated in Table 10 and FIGS. 5 and 6, within the first group, sample No. 73 appeared to be the most stable sample, in terms of the least change in color, in pH value, and in light absorbance. Also, with the second group, sample No. 75 appeared to be more stable than sample No. 74, in terms of the least change in color, in pH value, and in light absorbance. Again, the results suggest that 1% bisulfite and acidic pH contribute to the stability of the galactose injection solution.

EXAMPLE 6

Preparation of Galactose Injection Solution Sample Nos. 76–87

Sample Nos. 76–87 represent galactose injection solutions containing 40% by weight of galactose, with 0.025%, 0.01%, 0.05%, 0.5% or 1% by weight of sodium bisulfite, and with (1) 100 ml of distilled water (sample No. 76), (2) 0.01 M of triethanolamine (sample No. 77), and (3) 0.01 M citrate buffer (sample Nos. 78–87).

Sample Nos. 76–87 were prepared as follows:

1. Samples Nos. 76–87 were subdivided into 3 groups based on whether or not the galactose injection solution was in a buffer solution. In the case that the galactose injection was in a buffer solution, a further inquiry into the kind(s) of buffer solutions was conducted. The first group contained only 1 sample (sample No. 76), which contained 40% galactose in 100 ml of distilled water with no anti-oxidant. This sample was acted as a placebo control. The second group also contained only 1 sample (sample No. 77), which contained 40% galactose in 0.01 M triethanolamine buffer and 0.01% by weight of sodium bisulfite. The rest of the samples belonged to the third group, which contained 40% galactose in 0.01 M citrate buffer. Sample Nos. 78–79 further contained 1% bisulfite, with sample No. 78 at alkaline pH and sample No. 79 at acidic pH. Sample Nos. 80–81 further contained 0.05% bisulfite, with sample No. 80 at alkaline pH and sample No. 81 at acidic pH. Sample Nos. 82–83 further contained 0.025% bisulfite, with sample No. 82 at alkaline pH and sample No. 83 at acidic pH. Sample Nos. 84–85 further contained 0.01% bisulfite, with sample No. 84 at alkaline pH and sample No. 85 at acidic pH. Sample Nos. 86–87 further contained 0.1 % bisulfite, with sample No. 86 at alkaline pH and sample No. 87 at acidic pH..

2. Each of the galactose injection solutions described in (1) was autoclaved at 121° C., 1.2kg/cm$^2$ for fifteen (15) minutes.

3. Each of the galactose injection solutions described in (2) was stored in an oven at 80° C. for 2 weeks.

Results

Based on the results deduced from stability studies in sample Nos. 1–75, the ideal galactose injection solutions for 4% galactose should be in citrate buffer, containing relatively higher concentration of anti-oxidant such as sodium bisulfite (e.g., about 1% sodium bisulfite), and at an acidic pH.

Example 6 was designed to study the galactose injection solution when the galactose concentration was increased to 40%.

The results of the stability studies for sample Nos. 76–87 are shown in Table 11.

TABLE 11

Galactose Injection Solution Nos. 76–87.

| Formulation | 76 | 77 | 78 | 79 | 80 | 81 | 82 | 83 | 84 | 85 | 86 | 87 |
|---|---|---|---|---|---|---|---|---|---|---|---|---|
| galactose conc. % | 40 | 40 | 40 | 40 | 40 | 40 | 40 | 40 | 40 | 40 | 40 | 40 |
| Buffer | water | TEA | citr. | citr. | citr. | citr. | citr. | citr. | citr. | citr. | citr. | citr. |
| (M) | 100 ml | 0.01 | 0.01 | 0.01 | 0.01 | 0.01 | 0.01 | 0.01 | 0.01 | 0.01 | 0.01 | 0.01 |
| antioxidant (%) | | bisu. 0.01 | bisu. 1 | bisu. 1 | bisu. 0.05 | bisu. 0.05 | bisu. 0.025 | bisu. 0.025 | bisu. 0.01 | bisu. 0.01 | bisu. 0.5 | bisu. 0.5 |
| pH before sterilization | 3.98 | 7.24 | 8.49 | 4.31 | 7.86 | 4.47 | 7.87 | 4.48 | 7.22 | 4.49 | 8.29 | 4.50 |
| pH after sterilization | 4.70 | 6.78 | 8.47 | 4.29 | 7.78 | 4.33 | 7.30 | 4.52 | 6.85 | 4.53 | 8.29 | 4.52 |
| pH after 1 week | 3.59 | 4.33 | 5.01 | 3.70 | 4.57 | 4.30 | 4.69 | 4.17 | 4.76 | 4.34 | 4.45 | 4.00 |
| pH after 2 weeks | 3.2 | 3.67 | 4.40 | 3.61 | 4.22 | 4.01 | 4.16 | 4.11 | 4.29 | 4.13 | 4.11 | 3.62 |
| color change after 1 week | * | *** | ** | | *** | * | *** | * | *** | * | *** | |
| O.D. before sterilization | 0.201 | 0.184 | 0.083 | 0.047 | 0.167 | 0.164 | 0.173 | 0.169 | 0.186 | 0.178 | 0.112 | 0.062 |
| O.D. after sterilization | 0.219 | 0.627 | 1.810 | 0.063 | 0.259 | 0.220 | 0.269 | 0.196 | 0.223 | 0.221 | 1.208 | 0.090 |
| O.D. in the first week | 1.370 | 1.572 | 13.30 | 0.147 | 5.808 | 0.690 | 4.142 | 1.885 | 3.218 | 0.961 | 23.42 | 0.175 |
| O.D. in the second week | 3.647 | 5.352 | 50.74 | 0.204 | 13.28 | 1.781 | 21.76 | 4.890 | 10.95 | 3.581 | 60.72 | 0.294 |
| reason for rejection | color | color | color | | color | color | color | color | color | color | color | | conc. = concentration; TEA = triethanolamine buffer; citr. = citrate buffer; bisu. = sodium bisulfite;
*indicates the color changes: the more asterisks, the deeper the color.

As shown in Table 11, galactose degradation occurred in sample containing 40% galactose without any buffer solution or anti-oxidant, such as sample No. 76, as evidenced by the development of yellow color and sharp increase in light absorbance (an indication of increase in 5-HMF, the degradation product of galactose). Addition of 0.01 M triethanolamine and 0.01% sodium bisulfite (such as sample No. 77) to the 40% galactose injection solution did not improve the stability of the galactose injection solution.

When 0.01 M citrate buffer was added to the 40% galactose injection solution and the galactose injection solution was maintained at acidic pH, different concentrations of sodium bisulfite did not appear to affect the stability of the 40% galactose injection solution, as evidenced by the color change, the change in pH, and the change in light absorbance. In fact, when the sodium bisulfite concentration was at or above 0.5%, no color development in the 40% galactose injection solution was observed. However, if the 40% galactose injection solution in 0.01 M citrate buffer was maintained at alkaline pH, there was significant color development in samples after 1 week storage at 80° C. even in sample when the sodium bisulfite concentration is at or higher than 1%.

In conclusion, for 40% galactose injection solution, the optimal condition would be that the solution was in citrate buffer at acidic pH. Under this condition, the effect of sodium bisulfite on the galactose injection solution was minimal.

While the invention has been described with reference to the above specific embodiments, it is apparent that numerous modifications and variations can be made without departing from the scope and spirit of this invention. It is therefore intended that this invention be determined by the descriptions stated herein and the appended claims.

We claim:

1. A galactose injection solution comprising:
   1% to 50% by weight of galactose;
   a buffer solution; and
   an antioxidant;
   wherein said galactose injection solution is at pH 4.0 to 9.0.

2. The galactose injection solution according to claim 1, wherein said buffer solution is one selected from the group consisting of citrate buffer, phosphate buffer, acetate buffer, carbonate buffer, and triethanolamine buffer.

3. The galactose injection solution according to claim 1, wherein said buffer solution is citrate buffer.

4. The galactose injection solution according to claim 3, wherein said citrate buffer is at a concentration of 0.01 M to 1.0 M.

5. The galactose injection solution according claim 4, wherein said citrate buffer is at a concentration of about 0.01 M.

6. The galactose injection solution according to claim 1, wherein said antioxidant is sodium bisulfite or vitamin C.

7. The galactose injection solution according to claim 6, wherein said antioxidant is sodium bisulfite.

8. The galactose injection solution according to claim 7, wherein said anti-oxidant is at a concentration of 0.001 to 5% by weight.

9. The galactose injection solution according to claim 7, wherein said anti-oxidant is at a concentration of 0.01 to 1% by weight.

10. The galactose injection solution according to claim 1, wherein said galactose injection solution is at pH of about 4.5.

11. The galactose injection solution according to claim 1, wherein said galactose injection solution is at pH of about 7.4.

12. The galactose injection solution according to claim 1, wherein said galactose injection solution is stable at about 80° C. for about 2 weeks.

13. The galactose injection solution according claim 1, wherein said galactose injection solution is stable after sterilization by autoclaving.

* * * * *